United States Patent
Dukes-Dobos et al.

(10) Patent No.: US 6,581,677 B2
(45) Date of Patent: Jun. 24, 2003

(54) INFLATABLE MANNEQUIN AND SYSTEM FOR THERMAL PROPERTY MEASUREMENT AND ASSOCIATED METHODS

(75) Inventors: Francis N. Dukes-Dobos, Clearwater, FL (US); Uwe Reischl, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/930,114

(22) Filed: Aug. 15, 2001

(65) Prior Publication Data

US 2002/0062955 A1 May 30, 2002

Related U.S. Application Data

(60) Provisional application No. 60/225,606, filed on Aug. 15, 2000.

(51) Int. Cl.$^7$ .......................... G05D 23/00; G05D 16/00
(52) U.S. Cl. .................... 165/11.1; 165/46; 165/279; 2/DIG. 1; 2/DIG. 3; 607/104; 607/108; 62/259.3
(58) Field of Search .................... 165/46, 279, 11.1; 62/259.3; 607/96, 104, 108; 2/458, 2.11, 2.14, 2.15, 2.16, 7, DIG. 1, DIG. 3

(56) References Cited

U.S. PATENT DOCUMENTS

| | | |
|---|---|---|
| 2,693,088 A | 11/1954 | Green |
| 3,507,321 A | 4/1970 | Palma |
| 3,648,765 A | 3/1972 | Starr |
| 3,736,764 A | 6/1973 | Chambers et al. |
| 3,738,367 A | 6/1973 | Hardy |
| 3,743,012 A | 7/1973 | Laxo |
| 4,572,188 A * | 2/1986 | Augustine et al. ........ 165/46 X |
| 4,706,672 A * | 11/1987 | Jones ....................... 165/46 X |
| 4,747,408 A | 5/1988 | Chuan-Chih |
| 5,805,718 A | 9/1998 | Inoshiri et al. |
| 6,105,382 A * | 8/2000 | Reason ..................... 165/46 X |
| 2001/0049883 A1 * | 12/2001 | Ryden |

FOREIGN PATENT DOCUMENTS

| | | |
|---|---|---|
| DD | 138 825 A | 11/1979 |
| FR | 2 534 050 A1 | 10/1982 |
| GB | 2 191 884 A | 12/1987 |
| JP | 52-38951 | * 3/1977 |
| JP | 56108098 | 1/1983 |
| JP | 5-313759 | * 11/1993 |
| WO | WO 98/43080 | 10/1998 |

OTHER PUBLICATIONS

Holmér, I., "Thermal Manikins in Research and Standards," Proc. Third Intl. Mtg., *Thermal Manikin Testing 31 MM,* Eds. H. O. Nilsson and I. Holmér, pp. 1–7, 1999.

* cited by examiner

*Primary Examiner*—Ljiljana Ciric
(74) *Attorney, Agent, or Firm*—Anton J. Hopen; Smith & Hopen, P.A.

(57) ABSTRACT

A system for measuring a thermal property of a garment includes a mannequin having a form similar to at least a portion of a mammalian body and adapted to wear the garment. Fluid is circulatable through at least a portion of the mannequin. An outer surface temperature sensor is affixed to the mannequin, and a fluid pressure regulator and temperature controller are located exterior of the mannequin. A meter monitors the energy usage of the controller, which is indicative of the thermal property of the garment. Environmental conditions are controllable, including variable wind speeds and induced mannequin motion.

43 Claims, 3 Drawing Sheets under very dynamic scenarios. For example, it can be used to test a garment that has localized cooling, to determine the effectiveness of design concepts. Even though the localized cooling feature will reduce heat strain of the wearer, an important question is to what degree and where. This information is valuable in performing design trade-offs.

INFLATABLE MANNEQUIN AND SYSTEM FOR THERMAL PROPERTY MEASUREMENT AND ASSOCIATED METHODS

CROSS-REFERENCE TO RELATED APPLICATION

This application claims priority from provisional application 60/225,606, "Inflatable Mannequin, System, and Associated Methods," filed Aug. 15, 2000.

BACKGROUND OF THE INVENTION

1. Field of the Invention

The present invention relates to devices, systems, and methods for measuring thermal properties of clothing, and, more particularly, to such devices, systems, and methods for simulating a shape, size, and temperature of a human body.

2. Description of Related Art

Exposing a human being or other mammal to an extreme temperature environment, such as high heat levels, places it at risk for disorders and/or illnesses if the exposure exceeds their tolerance. The American Conference of Governmental Industrial Hygienists (ACGIH) has proposed a threshold limit value (TLV) for heat stress and strain, including safe tolerance limits for work in hot environments, which varies according to work intensity and thermal insulation of clothing. Clothing insulation is also an important factor in protection against cold. In addition, other thermal properties of clothing such as vapor permeability and ventilation also affect human heat tolerance.

At present there are two direct methods available for the measurement of the thermal properties of clothing such as insulation and ventilation. One method requires the use of an electronically instrumented mannequin, made of metal or plastic, that is placed inside a climatically controlled chamber, the cost of which is known at present to be approximately $1 million.

A second method requires human subjects to be exposed to high heat stress conditions inside a climatic chamber while exercising and carrying physiological monitoring equipment, including a rectal thermometer. This approach exposes test subjects to heat stress, discomfort, and health risks. Furthermore, because of individual variability, at least 12 test subjects are needed to provide sufficient statistics for such heat stress tests.

Ventilation of garments and breathability of the garment's material are key factors that allow metabolic heat to dissipate from a body. When garment ventilation is high, the insulation values of the protective clothing are of less significance. When the garment ventilation is low, however, the insulation value becomes very important.

Few countries around the world are believed to have laboratories where the testing of the thermal properties of protective garments can be performed using such sophisticated and expensive mannequins and instruments (Holmer and Ingar; *Thermal Manikins in Research and Standards*; Proceeding of the Third International Meeting of Thermal Manikin Testing, Oct. 12–13, 1999, the contents of which are incorporated herein by reference).

Among references known in the art, Green (U.S. Pat. No. 2,693,088) teaches an apparatus for conditioning compressed air to a flight suit, which regulates the circulating air to a desired temperature. The suit of Palma (U.S. Pat. No. 3,507,321) also provides temperature-regulated heating and/or cooling to all or part of a body. The space suit of Starr (U.S. Pat. No. 3,648,765) has a system for mixing warm and cold liquid to achieve temperature regulation. Chambers et al. (U.S. Pat. No. 3,736,764) disclose a fluid-cooled garment. The temperature of the coolant is based upon an evaporative water loss rate of the wearer. The hospital garment of Hardy (U.S. Pat. No. 3,738,367) has small-diameter tubes for conveying temperature-regulated fluid adjacent the body. Laxo (U.S. Pat. No. 3,743,012) teaches the use of counter-flow heat exchange to maintain an equal temperature distribution along the inner surface of a garment for use by, for example, a diver. The garment of Chuan-Chih (U.S. Pat. No. 4,747,408) provides the wearer with a portable sauna by alternately delivering hot air and cooled water to the garment. Inoshiri et al. (U.S. Pat. No. 5,805,718), in the process of determining an amount of clothing being worn by a subject, calculate the heat discharged out of the clothing and the thermal resistance of the clothing.

SUMMARY OF THE INVENTION

It is therefore an object of the present invention to provide a device, system, and method for measuring the thermal properties of clothing.

It is an additional object to provide such an invention that is significantly less costly than previous devices and systems.

It is a further object to provide such an invention that simulates a plurality of properties of a mammalian body.

It is another object to provide a system and method for measuring clothing insulation.

It is yet an additional object to provide such a system and method for measuring vapor permeability of a garment.

It is yet a further object to provide such a system and method for measuring the ventilation of the garment and the breathability of a garment's material.

It is yet another object to provide a device, system, and method for improving the safety of mammals exposed to high temperatures.

A specific object is to provide such an invention for improving worker safety in high-temperature environments.

These objects and others are attained by the present invention, one aspect of which comprises a device for measuring a thermal property of a garment. The device comprises a mannequin having a form similar to at least a portion of a mammalian body. The mannequin is adapted to wear a garment for which it is desired to have a thermal property measured.

The device further comprises fluid circulating means for receiving a fluid therethrough having an inlet and an outlet. The fluid circulating means is positioned to travel through at least a portion of the mannequin. Means for sensing a temperature and for maintaining a desired temperature of the fluid are located at at least one location exterior of the mannequin. The desired temperature is preferably similar to that of the skin of the mammalian body being simulated.

Throughout the present application, the word fluid is not intended as a limitation, and is used to signify any medium that satisfies a requirement for heat transfer as well as allowing the system to maintain constant pressure, including fluids such as water, gases such as nitrogen, mixtures of gases such as air, or combinations or suspensions such as fine particulates in air.

The system for measuring a thermal property of a garment comprises a mannequin as above. Means are provided for circulating a fluid through at least a portion of the mannequin, for controlling a temperature of the fluid being circulated for simulating a skin temperature of the mammalian body, for sensing a temperature at at least one location exterior of the mannequin beneath the garment, and for monitoring an energy usage required to control the fluid temperature. The energy usage is indicative of the thermal property of the garment.

A method for measuring a thermal property of a garment comprises the steps of placing a mannequin as above in a desired environment and channeling a fluid through at least a portion of the mannequin and establishing a control value. Next a garment for which it is desired to have a thermal property measured is placed onto the mannequin, and a change in the electrical energy is determined.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

Figure 2:
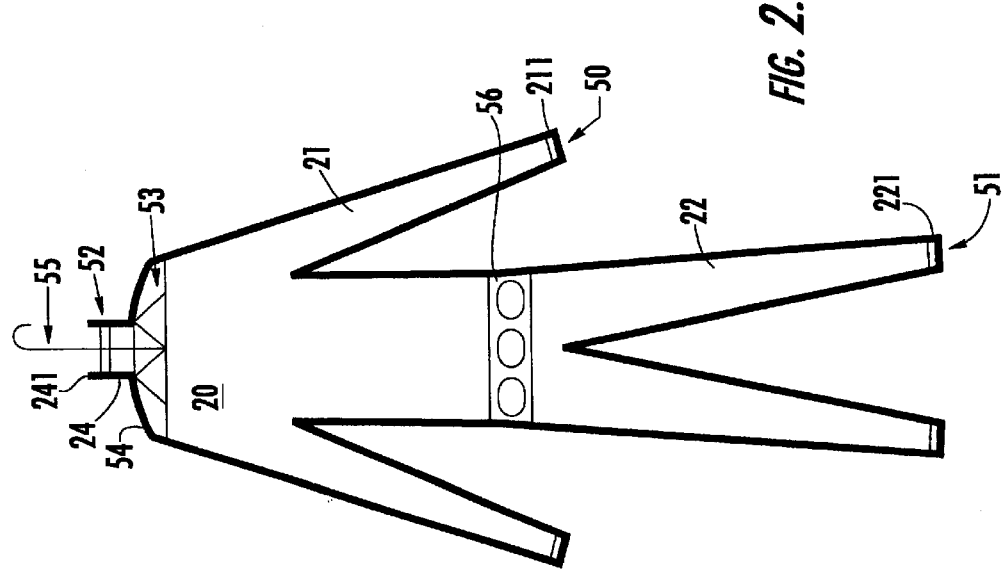
FIG. 2 illustrates the suspension system for the mannequin.

A description of the preferred embodiments of the present invention will now be presented with reference to FIGS. 1–4.

An exemplary system 10 of the present invention (FIG. 1) comprises a device, which in a preferred embodiment comprises a light-weight, flexible, inflatable, and fluid-tight mannequin 20 adapted to resemble a medium-sized adult male or female human body without a head. In a most preferred embodiment, the mannequin 20 further has no hands or feet (or, in the case of another mammal, equivalent coverings for analogous body parts such as paws or tail). This embodiment is not intended as a limitation, however, as it may be conceived by one of skill in the art that other body forms may be included within the scope of the invention, such as a child or an animal, or a body with head, hands, feet, or any combination thereof.

The mannequin 20 is substantially hollow in a preferred embodiment, although this is not intended as a limitation, and a unit having solid portions may also be contemplated. The mannequin 20 has a pair of arms 21, a pair of legs 22, and an opening 23 at the neck 24. Testing includes placing the mannequin 20 within a desired environment, first unclad and then clad with a garment 90 desired to be tested for at least one thermal property. Such a garment 90 may include, for example, clothing designed for use in ranges of environments, such as temperatures, ranges of wind speeds, ranges of humidity, ranges of pressures, ranges of irradiance, and any other combination of environmental conditions. The garment 90 may also be contemplated for use in normal ranges of environmental conditions, but wherein the simulated body is undergoing a stressor on its internal conditions, such as exercise or a fever. Likewise a person of skill in the art will recognize that combinations of these conditions may be simulated, and the invention is not intended to be limited to any particular condition or testing regime.

The mannequin 20 may comprise any suitable material known in the art durable in the range of temperatures desired to be tested. Some factors, individually or in various combinations, that can be considered in selecting suitable materials are flexibility, tolerance of environmental testing conditions, light weight, heat resistance, and ability to maintain a seal. A person of skill in the art will recognize that materials such as plastics and rubber can be used. In a particular embodiment, the mannequin 20 may comprise a disposable material such as some type of plastic or a combination of material, although this is not intended as a limitation.

The fluid circulation means in this embodiment comprises an insulated introducing tube 25 that enters through the neck opening 23, which is otherwise hermetically sealed, and has a plurality of openings 26 along a portion inside the mannequin 20 for introducing fluid, here air, therewithin. A plurality of return tubes 27, here four, extend inside the mannequin 20, one along each limb 21,22. Each return tube 27 has an opening at a distal end 28, so that air entering through the introducing tube 25 circulates through the mannequin's interior and exits by entering the return tubes' distal ends 28. Preferably the arms 21, legs 22, and neck 24 have attached thereto detachable airtight closures 50,51,52, respectively, at their distal ends 211,221,241, to facilitate installation and maintenance of the tubing system (FIG. 2).

Each return tube's proximal end 29 joins a manifold 30 outside the mannequin 20, an insulated exterior return tube 31 leading from which enters a temperature and pressure control unit 32, from which in turn exits air to join the introducing tube 25. The control unit 32 comprises a substantially hollow enclosure having an inlet 33 for joining with the exterior return tube's proximal end 34 and an outlet 35 for joining with the introducing tube's proximal end 36. The temperature and pressure control unit 32 in system 10 is preferably housed in a thermally insulated enclosure Inside the control unit 32 is housed a fan 37. Between the inlet 33 and the fan 37 is an opening 38 in fluid communication with a fluid pressure regulator, here, an air pressure regulator 39, which is adapted to maintain the pressure within the mannequin 20 and control unit 32 at a desired substantially constant value. Preferably the pressure should be maintained sufficiently high to preserve a desired shape of the mannequin 20 after addition of the garment 90.

Between the fan 37 and the outlet 35 is positioned a heating coil 40, which is in electrical communication with a watt meter 41 and is under control of a thermostat controller 42. The thermostat controller 42 is responsive to a signal from a surface temperature sensor integrator 43, which in turn receives input from a plurality of sensors 44 affixed exterior of, here, against the outside of, the mannequin 20. In a preferred embodiment there are 15 sensors 44 positioned at 15 locations, in accordance with the ASTM standard, or other locations necessary to determine the mean surface temperature, although these numbers are not intended as limitations.

The fluid/air temperature of the system 10 is regulated by an interplay between the sensing and control components: The sensors 44 determine a temperature of the mannequin's surface, which is relayed to the integrator 43, which in turn determines a mean surface temperature. This then signals the thermostat controller 42 to regulate the heating level of the heating coil 40 to thereby control the temperature of the air exiting the control unit 32.

The watt meter 41 is adapted to measure the electrical energy consumed by the heating coil 40, which reflects the magnitude of the garment's insulation when compared against control values of a mannequin 20 without a garment 90.

An exemplary support system for retaining the mannequin's shape in a desired orientation (FIG. 2) comprises a frame 53 adapted for placement within the mannequin 20 at the shoulders 54. The frame 53, not unlike a clothing hanger in this embodiment, has a hook 55 attached thereto extending out of the neck opening 23 to permit hanging the mannequin 20 therefrom. Other types of framing may also be contemplated, whether in addition to or instead of the foregoing.

The support system further comprises a semirigid waistband 56 affixed generally around the mannequin's waist, which permits the donning of belts and/or waistbands for pants and skirts without substantially altering the shape of the mannequin 20. Other types of support may also be contemplated, whether in addition to or instead of the foregoing.

In a first embodiment of a method of using the system 10 the mannequin 20 is placed into a room or enclosure wherein the air temperature, air movement, and humidity are maintained at a substantially constant level. It is to be understood by one of skill in the art that the room or enclosure utilized in the present invention does not need to comprise a climate control chamber such as is known in the art, permitting a substantially reduced cost of operation for the present invention. The heating system is activated when the mannequin 20 is unclothed, and the average surface temperature of the mannequin 20 is adjusted to simulate that of human (or other homeothermic mammal) skin and is maintained at this level automatically throughout the measurement period, while collecting watt meter 41 data.

The garment 90 to be tested is then put on the mannequin 20 and the watt readings recorded with the watt meter 41. The differences between the unclothed and clothed conditions provide quantitative information on the garment's insulation properties. The breathability of the garment's fabric can also be determined separately by first closing the ventilation openings of the garment, such as at the arms, the legs, and the neck.

Tests may be conducted under a plurality of conditions, such as under varying wind speed (FIG. 3) to determine ventilation characteristics. Arm 21 and leg 22 motion can be added to measure the effects of walking on garment insulation and ventilation. In addition, the mannequin's surface could be wetted to determine the effects of garment vapor permeability and insulation on sweat evaporation or under precipitation conditions.

The method of using the system 10 of the present invention (FIG. 3) to simulate walking includes attaching a bracket 57 to the distal ends of each arm 21 and leg 22. The bracket 57 is adapted to have affixed thereto a push-pull rod 58 or wire for moving the arms 21 and legs 22 backwards and forwards to simulate a walking motion with the use of an effector. The method to simulate wind may comprise introducing air flow using an air fan 59 under speed control by controller 60, which permits measurement of the ventilation properties of the garment 90 at different air velocities.

An alternate embodiment (FIG. 4) of the system 10' comprises an alternate mannequin 20', here having a complete set of extremities, including head 61, hands 62, and feet 63. It will be understood that the mannequin also may contain only some of these parts. The control, sensing, and fluid circulation systems are contemplated as remaining substantially the same as those of FIG. 1, although this is not intended as a limitation. A plurality of subsystems can also be utilized. For example, different parts of the mannequin, such as the hands or other extremities, can be connected to separate circulation or control systems. The opening 23' for passing tubes 25 and 27 therethrough is illustrated here as in the shoulder region, although this is not intended as a limitation, and one of skill in the art will appreciate that such an opening 23' may be placed in any convenient location.

Figure 1:
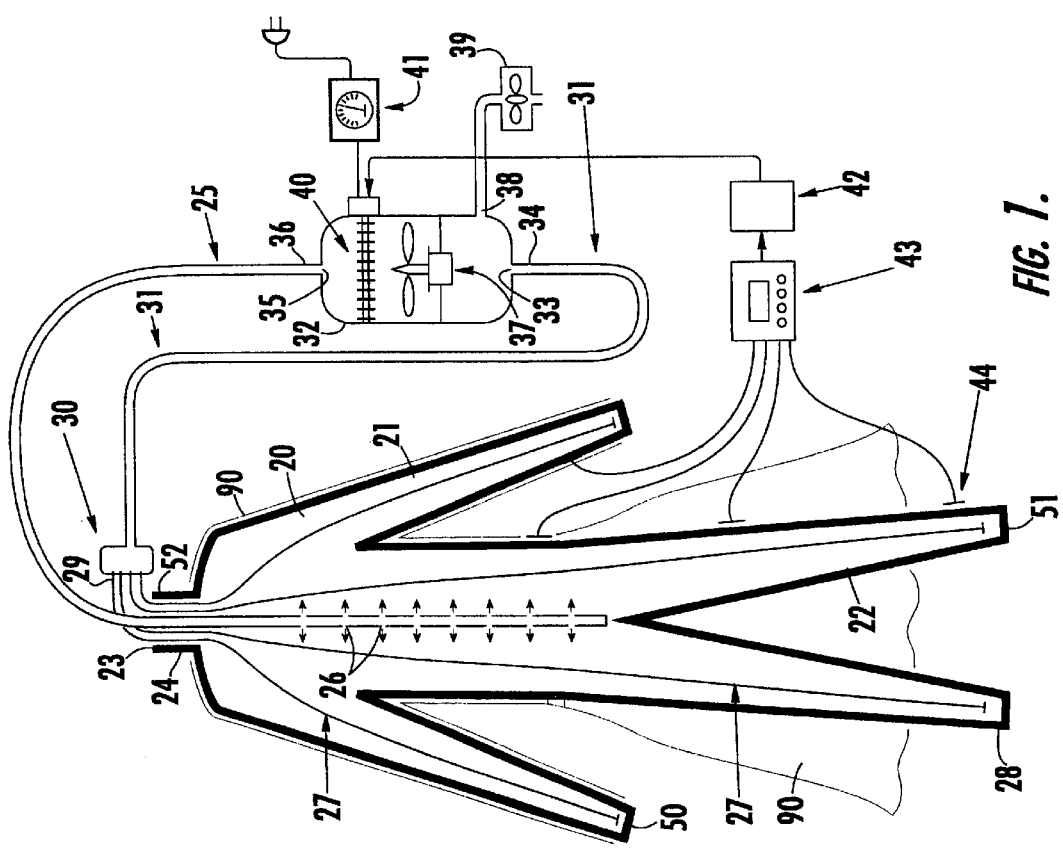
FIG. 1 illustrates the garment thermal property measurement system of the present invention.
Figure 3:
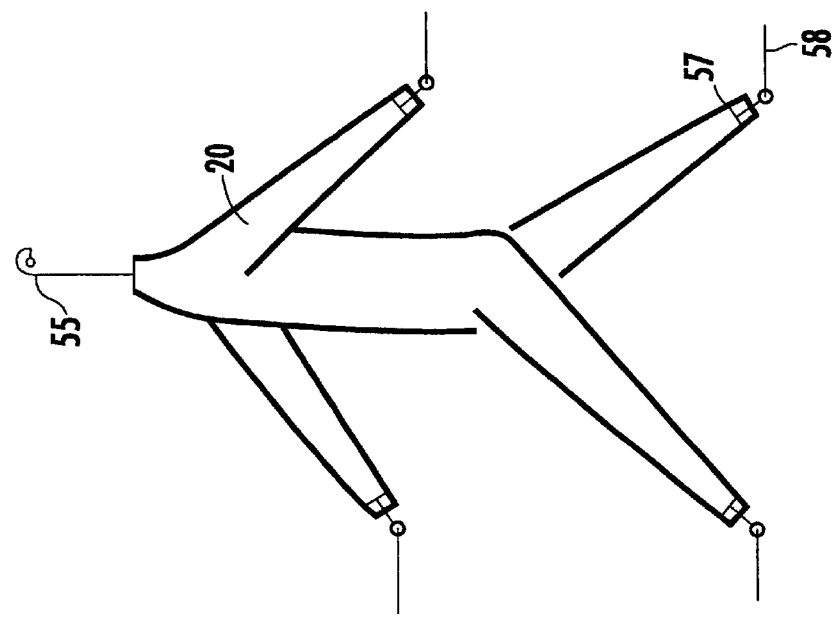
FIG. 3 illustrates the system for measuring air-flow effect on clothing ventilation.
Figure 3:
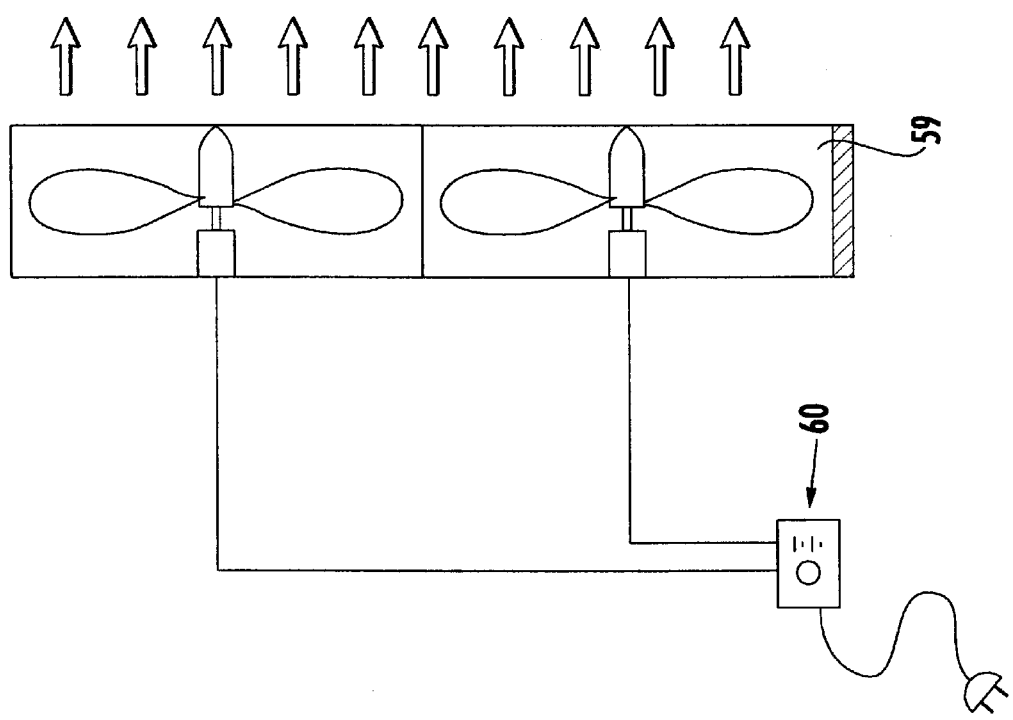
Figure 4:
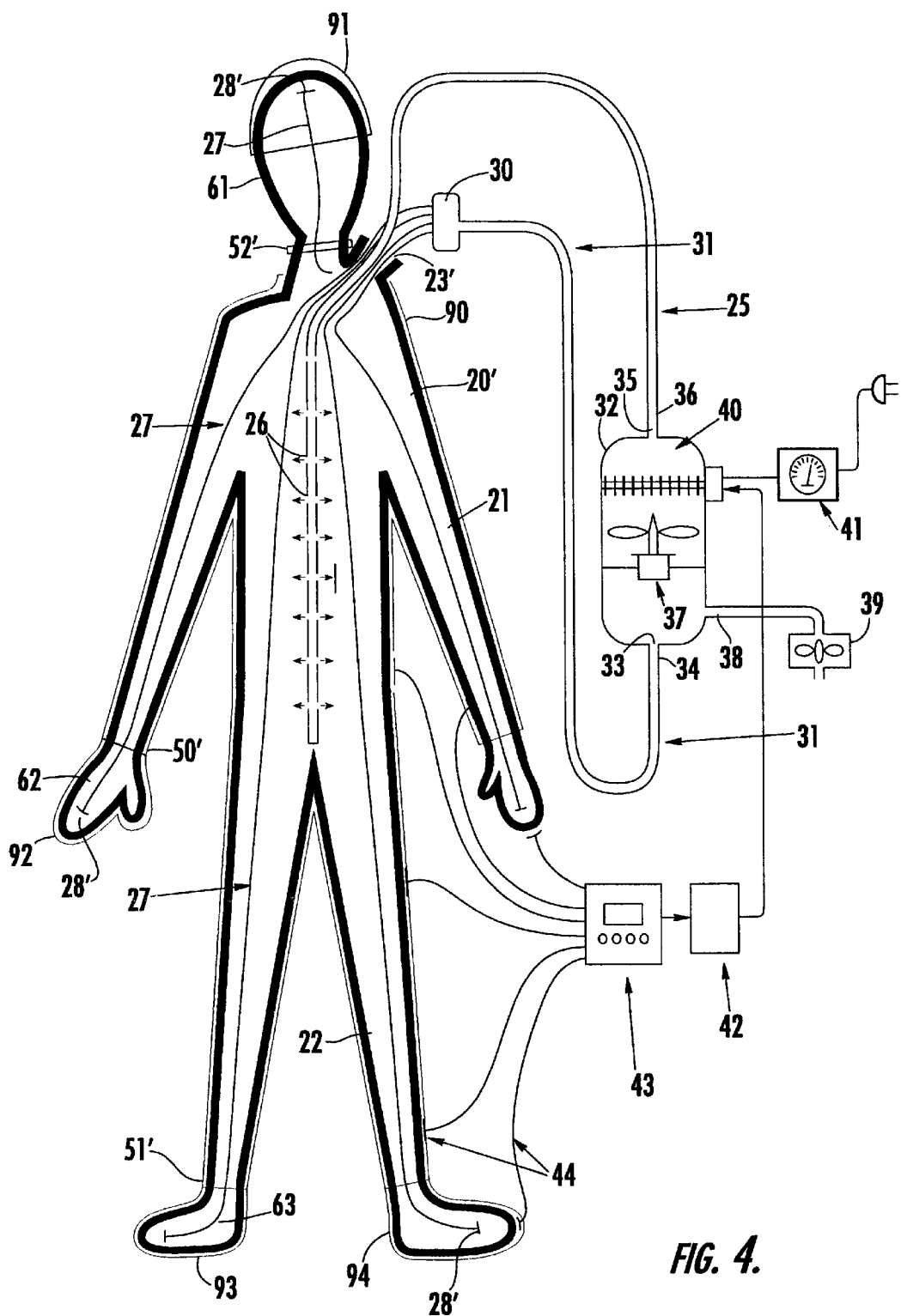
FIG. 4 illustrates an alternate embodiment of a garment thermal property measurement system.

This system 10' is amenable for testing an all-encompassing garment, such as a body suit, jump suit, uniform, or a space suit, a plurality of garments, such as a hat 91, gloves 92, socks 93, or footwear 94, or an unfinished garment or fabric, in similar fashion to the embodiment of FIG. 1. Here the distal ends 28' of the return tubes 27' are preferably located adjacent distal ends of the extremities. Airtight closures 50',51',52' may also be provided, here shown being used to affix the hands 62, feet 63, and head 61, to the body, although other affixing methods may be contemplated.

It may be appreciated by one skilled in the art that additional embodiments may be contemplated, including various shapes of mannequins for simulating different animals, mannequins having only a part of a body, such as a torso only, head only, limb only, or any combination thereof, and the use of different circulating fluids and fluid circulation and control systems. One of skill in the art will also appreciate that different control systems, such as for pumping and heating, are required for different chosen circulating media.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

What is claimed is:

1. A system for measuring thermal property of a garment comprising:
   a garment;
   a mannequin having a hollow interior space and having a substantially mammalian form, the mannequin wearing the garment means for circulating a fluid through at least a portion of the mannequin covered by the garment;
   means for sensing the mannequin outer surface temperature at at least one location beneath the garment;
   means for controlling the temperature of the fluid being circulated for maintaining a substantially constant mannequin outer surface temperature;
   means for controlling the pressure of the fluid being circulated; and
   means for monitoring the energy usage of the temperature controlling means for determining the thermal property of the garment.

2. The system recited in claim 1, wherein the mannequin comprises a substantially human form.

3. The system recited in claim 1, wherein the fluid-circulating means comprises means for circulating a gas.

4. The system recited in claim 3, wherein the gas-circulating means comprises means for circulating air.

5. The system recited in claim 1, wherein the fluid-circulating means comprises introducing tubing having an inlet and an outlet, the outlet in fluid communication with the interior space of the mannequin, and the pressure control means in fluid communication with the tubing inlet.

6. The system recited in claim 5, wherein the fluid-circulating means further comprises return tubing having an inlet and an outlet, the inlet in fluid communication with the interior space, of the mannequin the outlet in fluid communication with the pressure control means.

7. The system recited in claim 6, wherein the return tubing inlet is positioned adjacent a first extremity of the mannequin and the introducing tubing outlet is positioned within the interior space of the mannequin in spaced relation from the first extremity.

8. The system recited in claim 7, wherein the mannequin comprises a substantially human form having two arms and two legs, the first extremity comprises at least one of a distal end of an arm and a leg and the introducing tubing outlet comprises a plurality of openings.

9. The system recited in claim 8, wherein the return tubing comprises four tubes, one tube extending along each arm and each leg.

10. The system recited iii claim 6, wherein the return tubing comprises a plurality of return tubes, each having an opening at a distal end comprising the inlet and at a proximal end comprising the outlet, the system further comprising:
a manifold for uniting fluid exiting from the return tubes;
a control unit for maintaining fluid pressure at a desired level, the control unit having an inlet in fluid communication with an outlet of the manifold; and
an exterior return tube for establishing flui4 communication between an outlet of the control unit and the introducing tubing inlet.

11. The system recited in claim 10, wherein the fluid pressure regulator is for maintaining a desired shape of the mannequin, and the control unit further comprises means for facilitating a movement of fluid toward the introducing tubing inlet.

12. The system recited in claim 11, wherein the fluid pressure regulator comprises an air pressure regulator, and the facilitating means comprises a fan downstream of the air pressure regulator.

13. The system recited in claim 10, wherein the temperature controlling means is housed within the control unit and comprises heating means, the energy usage monitoring means comprises an energy meter in electrical communication with the heating means, and a thermostat controller in controlling relation to the heating means.

14. The system recited in claim 13, wherein the mannequin outer surface temperature sensing means comprises a sensor in signal communication with the thermostat controller.

15. The system recited in claim 14, wherein the sensor comprises a plurality of sensors affixed in spaced relation from each other to the mannequin outer surface, and wherein the system further comprises a sensor integrator in signal communication with the plurality of sensors for determining a mean outer surface temperature of the mannequin.

16. The system recited in claim 14, wherein the energy meter measures an energy consumed by the heating means for measuring an insulating property of the garment relative to a predetermined control value.

17. The system recited in claim 1, further comprising means for supporting the mannequin in a desired orientation.

18. The system recited in claim 17, wherein the form comprises a substantially human form having a torso, and the supporting means comprises a frame positionable within the mannequin at a shoulder region thereof, the frame comprising a hook extending out of the mannequin for hanging the mannequin therefrom.

19. The system recited in claim 17, wherein the form comprises a substantially human form, and the system further comprises a substantially rigid waistband for retaining a shape of the mannequin in a waist region thereof.

20. The system recited in claim 1, further comprising variable means for creating an air current outside the mannequin, for simulating wind velocities.

21. The system recited in claim 1, wherein the mannequin comprises a plurality of limbs, and the system further comprises means for moving the limbs to simulate a desired mannequin activity for testing an effect of the activity upon the thermal property.

22. A device for measuring a thermal property of a garment comprising
a garment;
a mannequin having a substantially human shape, the mannequin wearing the garment;
means for circulating a fluid through at least a portion of the mannequin covered by the garment;
means for sensing the mannequin outer surface temperature;
means for supporting the mannequin in a desired orientation; and
a substantially rigid waistband for retaining the shape of the mannequin at a waist region of the mannequin.

23. The device recited in claim 22, wherein the mannequin comprises a substantially human form having two arms, two legs, and a neck having an opening into an interior of the mannequin.

24. The device recited in claim 23, wherein the circulating means comprises:
introducing tubing for receiving fluid into an inlet and for introducing fluid into the mannequin interior from an interior portion, the interior portion having a plurality of openings therethrough; and
a plurality of return tubes, one tube extending along each arm and each leg, each return tube having an inlet positioned within the mannequin in spaced relation from the interior portion openings and an outlet at a distal end thereof.

25. The device recited in claim 23 wherein the form comprises a substantially human shaped torso and the supporting means comprises a frame positionable within the mannequin at a shoulder region thereof the frame comprising a hook extending out of the mannequin for hanging the mannequin.

26. The device recited in claim 23, wherein the system further comprises a substantially rigid waistband for retaining the shape of the mannequin in a waist region defined by the substantially human form.

27. The device recited in claim 22, further comprising means for supporting the mannequin in a desired orientation.

28. A method for measuring a thermal property of a garment comprising the steps of:
providing a garment;
placing a hollow mannequin having an interior space in a desired environment, the mannequin having a substantially mammalian shape;

introducing fluid into the interior space of the mannequin and circulating the fluid trough at least a portion of the mannequin coverable by the garment;

regulating the pressure of the fluid;

sensing the mannequin outer surface temperature at at least one location;

controlling the temperature of the fluid being circulated to maintain a substantially constant mannequin outer surface temperature;

monitoring the energy usage of the temperature controlling step;

placing the garment onto the mannequin;

sensing the mannequin outer surface temperature at at least one location beneath the garment;

continuing to control the temperature of the fluid being circulated to maintain a substantially constant mannequin outer surface temperature; and monitoring the energy source of the temperature controlling step for calculating thermal property from a difference between the energy usage with and without the garment being on the mannequin.

29. The method recited in claim 28, wherein the fluid-circulating step comprises circulating a gas.

30. The method recited in claim 29, wherein the gas-circulating step comprises circulating air.

31. The method recited in claim 28, wherein the fluid-circulating step comprises introducing fluid into an interior space of the mannequin, and regulating a pressure of the fluid.

32. The method recited in claim 28, wherein the fluid-circulating step further to rises returning fluid from the mannequin interior space.

33. The method recited in claim 32, wherein the fluid returning step comprises taking fluid from adjacent a first extremity of the mannequin and the fluid introducing step comprises introducing fluid into an interior space of the mannequin in spaced relation from the first extremity.

34. The method recited in claim 33, wherein the mannequin comprises a substantially human form having two arms and two legs, the first extremity comprises at least one of a distal end of an arm and a leg.

35. The method recited in claim 32, wherein the fluid returning step comprises returning fluid from four locations, one adjacent a distal end of each arm and each leg.

36. The method recited in claim 32, wherein the fluid returning step comprises returning fluid via a plurality of return tubes, and uniting fluid exiting from the return tubes proximal ends at an inlet thereof; and further comprising the step of maintaining fluid pressure at a desired level.

37. The method recited in claim 36, wherein the fluid pressure maintaining step comprises maintaining sufficient pressure to maintain a desired shape of the mannequin.

38. The method recited in claim 28, wherein the temperature controlling step comprises heating the fluid, the energy usage monitoring step comprises metering the heating step, and further comprising the step of controlling the heating step responsive to the sensing step.

39. The method recited in claim 38, wherein the mannequin outer surface temperature sensing step comprises sensing the mannequin outer surface temperature at a plurality of locations, integrating the sensed outer surface temperatures, and sending a signal representative thereof to control the heating step.

40. The method recited in claim 28, further comprising the step of supporting the mannequin in a desired orientation.

41. The method recited in claim 28, further comprising creating an air current outside the mannequin, for simulating wind velocities.

42. The method recited in claim 28, wherein the mannequin comprises a plurality of limbs, and the further comprising moving the limbs to simulate a desired mannequin activity and testing an effect of the activity upon the thermal property.

43. A method for measuring a thermal property of a garment comprising it the steps of:

providing a garment;

placing a mannequin in a desired environment, the mannequin having a substantially mammalian shape;

placing the garment onto the mannequin;

circulating fluid through at least a portion of the mannequin covered by the garment;

sensing the mannequin outer surface temperature at a plurality of locations beneath the garment;

integrating the sensed outer surface temperatures and generating a control signal;

controlling the temperature of the fluid being circulated to maintain a substantially constant mannequin outer surface temperature by heating or cooling the fluid in response to information contained in the control signal;

monitoring the energy usage of the heating or cooling step to calculate the thermal property fronts difference between the energy usage and a predetermined control energy usage value obtained.

\* \* \* \* \*